United States Patent [19]

Potter et al.

[11] Patent Number: 5,766,207
[45] Date of Patent: Jun. 16, 1998

[54] DRIVER AND METHOD FOR DRIVING PNEUMATIC VENTRICULAR ASSIST DEVICES

[75] Inventors: David Stuart Potter, Cowes; Dereck Ronald Wheeldon, Christchurch; Terrence Michael McCarthy, Durham; Charles David Ogilvy Potter, Oxford, all of England

[73] Assignee: Thoratec Laboratories Corporation, Berkeley, Calif.

[21] Appl. No.: 702,593

[22] PCT Filed: Mar. 6, 1995

[86] PCT No.: PCT/GB95/00482

§ 371 Date: Dec. 23, 1996

§ 102(e) Date: Dec. 23, 1996

[87] PCT Pub. No.: WO95/23621

PCT Pub. Date: Sep. 8, 1995

[30] Foreign Application Priority Data

Mar. 4, 1994 [GB] United Kingdom .................. 9404321

[51] Int. Cl.$^6$ .................................................. A61M 1/10
[52] U.S. Cl. ................................................... 600/16
[58] Field of Search ................................... 600/16–18

[56] References Cited

U.S. PATENT DOCUMENTS

| 3,449,767 | 6/1969 | Bolig | 600/16 |
|---|---|---|---|
| 3,674,381 | 7/1972 | Schiff . | |
| 4,597,381 | 7/1986 | Oum et al. | 600/16 |
| 4,942,735 | 7/1990 | Mushika et al. . | |
| 4,969,866 | 11/1990 | Inagaki | 600/18 |
| 5,282,849 | 2/1994 | Kolff et al. . | |
| 5,380,267 | 1/1995 | Boutelle et al. | 600/18 |

FOREIGN PATENT DOCUMENTS

| 0542383 | 5/1993 | European Pat. Off. | 600/16 |

*Primary Examiner*—William E. Kamm
*Attorney, Agent, or Firm*—Alix, Yale & Ristas, LLP

[57] ABSTRACT

A driver for at least one pneumatically-actuated ventricular assist device (VAD), includes a portable housing which encloses a single pump for performing blood-filling and blood-emptying operations of the VAD, a switching valve for alternately communicating the inlet and outlet of the pump with the VAD, a vacuum relief device for subjecting the VAD to negative pressure when performing blood-filling, a battery, and a controller for controlling operation of the driver. The use of a single pump enables the driver to be fully portable. A novel blood pumping system and a method of using the same are also disclosed.

21 Claims, 1 Drawing Sheet

U.S. Patent    Jun. 16, 1998    5,766,207
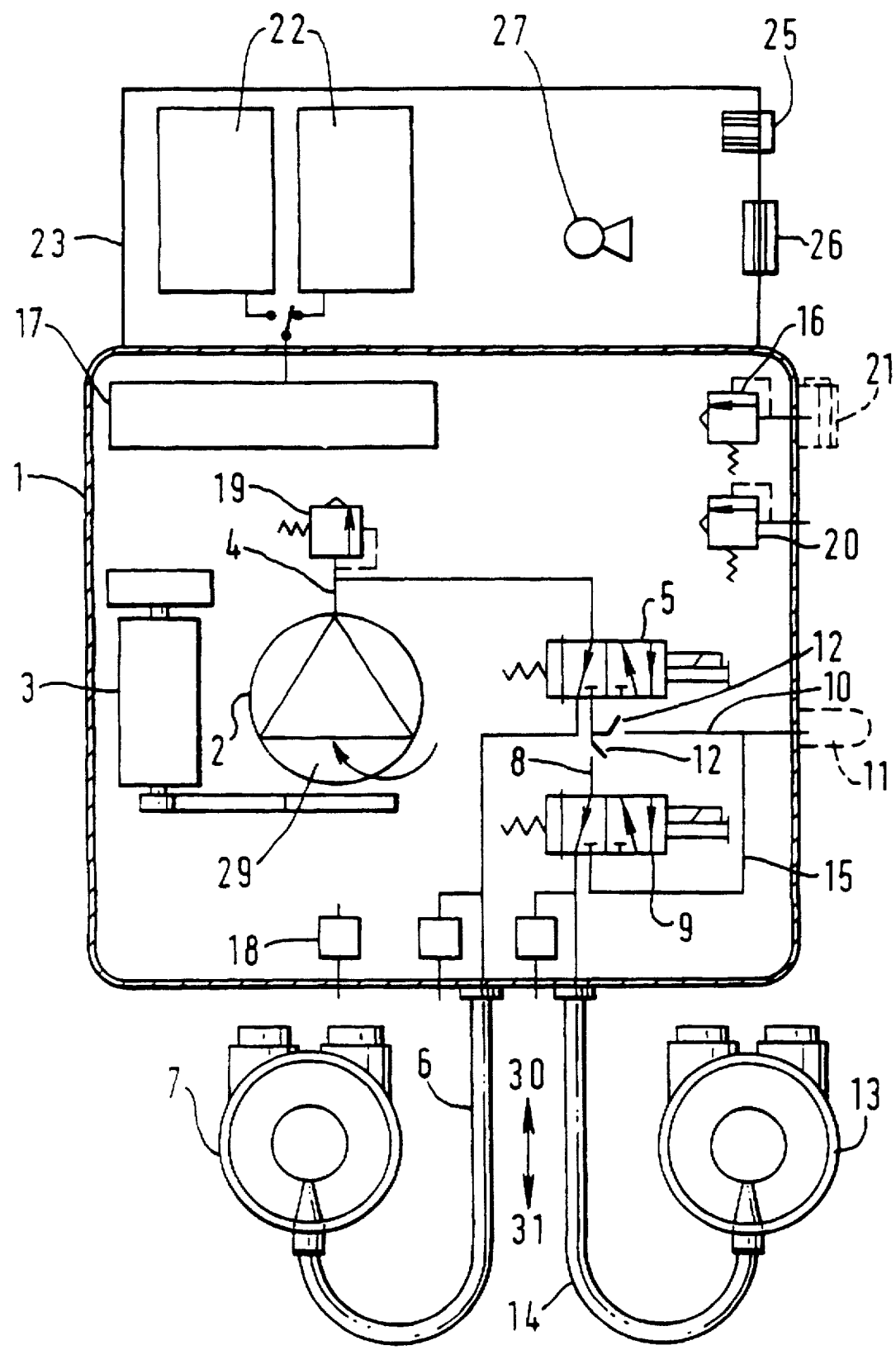

DRIVER AND METHOD FOR DRIVING PNEUMATIC VENTRICULAR ASSIST DEVICES

The present invention relates to equipment for, and methods for, driving pneumatically-operated apparatus such as pneumatically-actuated ventricular assist devices (commonly known as, and hereinafter called "VADs").

VADs are fitted to patients either singly (in a majority of cases) or as a pair to help the natural heart perform its blood circulation functions. The VADs can be located either paracorporeally or they can be implanted within the body; in either case suitable connections are made to the circulatory system of the patient.

VADs are used typically to support a patient recovering after surgery, or, in the case of heart failure, for example, to provide support to patients to enable them to maintain health whilst they are awaiting transplant surgery. In the latter case in particular, the VAD may be fitted to a patient for weeks or even months, until a suitable donor becomes available.

A pneumatically-actuated VAD may comprise a diaphragm-type or sac-type blood pump which is powered by subjecting the membrane separating a blood space from a gas space alternately to a forward flow of pressurised gas, such as air, for emptying blood from the VAD (systole), and to a reverse flow of exhaust gas under suction or partial vacuum pressure for inducing blood back into the VAD (diastole) to fill it in preparation for the next emptying phase. Thus, the VAD can be used either to pump blood in parallel (synchronously) with the heart, or in counter pulsation with the heart.

The operation of the pneumatic VAD is controlled by gas flow to and from its gas space via a gas supply line to subject the membrane alternately to a positive pressure (blood-emptying) and then to a partial vacuum pressure or negative pressure (blood-filling). This is achieved by connecting the VAD by means of suitable valves and tubing alternately to a source of high pressure gas and to a partial vacuum with means for controlling the flow. The rate of switching between alternate connections and the duration of each connection is controlled by a suitable microprocessor to provide the required blood pumping operation.

In prior art systems, the sources of high pressure and the partial vacuum (negative pressure) are provided in the form of reservoir gas tanks at high pressure, and at partial vacuum, respectively. Most commonly two separate pumping systems are used, which respectively maintain each reservoir at the appropriate pressure. Further, back-up sources of pressure, such as compressed gas cylinders, may also be provided.

Each pumping system, which can comprise one or more pumps or compressors, may be electrically driven and requires a battery or mains power source. The inlet of one pumping system may be used to establish a partial vacuum to be communicated to the VAD with the outlet of that pumping system typically being vented to the atmosphere. The outlet of the other pumping system may be used to establish a high pressure to be communicated to the VAD, typically with its inlet being open to the atmosphere.

Common driving equipment for operating a VAD therefore includes at least two gas reservoirs, two pumping systems (one for each reservoir), a power source, and the appropriate controller (control electronics). This equipment is typically contained in a separate housing which may be positioned beside the patient, and is connected to the VAD by means of suitable gas supply lines.

However, it is in many cases desirable for a patient to be able to move around on their own as easily as possible. This is especially true of patients wearing VADs for long periods of time who may otherwise be fit enough to leave their beds, for example, but are hindered by the need to take with them at all times the driver equipment for the VAD. In view of this, attempts have been made to make VAD drivers portable, so as to improve the patient's quality of life. To this end, the driver consoles have been placed on wheels such that the patient, or a helper, can wheel the driver console around as the patient moves. However, the driver's portability is constrained by the size and weight of the pumping system, the gas reservoirs, the battery power sources, etc., and the need to wheel the console and, thus, although some relative portability is achieved, improvement is desired.

According to a first aspect of the present invention, there is provided a driver for at least one pneumatically-actuated ventricular assist device (VAD), comprising a portable housing, the housing mounting: a single pump arranged to generate gas flow for performing both the blood-filling and the blood-emptying operations of the at least one VAD, a switching valve for alternately communicating the inlet and outlet of the pump with the at least one VAD, vacuum relief means also communicating with the inlet of said pump so that the at least one VAD is subjected to a predetermined negative pressure when performing blood-filling, and a controller for controlling the operation of the driver.

The use of a common pump to generate gas flow for both blood-emptying and blood-filling of the VAD greatly enhances the portability of the driver. Thus, in contrast to prior art drivers, the gas supplied to the VAD by the pump is, after blood-emptying, returned to the inlet of the same pump during blood-filling, rather than to a second, independent pump. As only a single pump is required, the size and weight of the driver may be greatly reduced. Furthermore, a single pump having only a single drive motor requires less power in use, and eliminates the additional power losses which are associated with the use of a second pump. This enables smaller and fewer batteries to be used, thus saving more weight and space.

The preferred driver of the present invention is, therefore, sufficiently lightweight and small to be readily portable. It is therefore mounted on a housing which carries all the driver equipment including the pump; controller, e.g. an electronic controller or microprocessor; and necessary valves, in order to enable it to moved by the patient easily, thus providing a fully portable system. The patient, therefore has more freedom of movement and greatly improved quality of life. A power source for the driver, e.g. a battery, is also preferably mounted on the housing.

In use, it may be that patients will require some form of assistance in moving the VAD driver particularly in the early phase of recovery, which assistance could be provided for example by a second person carrying the driver or some form of wheeled transport for the driver. However, once the patient has regained sufficient strength, it is preferred for the driver to be carried by the patient themselves to provide independent mobility. Thus the driver (i.e. housing) could be mounted on a wheeled hand-cart or trolley to allow it to be moved, but the housing is most preferably adapted to be carried by a patient.

In the latter case, the housing may be any suitable housing for mounting the driver which can be carried by a patient. The housing may be provided with straps to allow it to be carried or can be in the form of, or within, a bag having straps to enable a patient to carry or wear it.

The vacuum relief means effectively acts to provide a secondary gas source to the pump inlet, in addition to the gas contained in the VAD and associated tubing. This ensures that the VAD membrane is not subjected to excessively low pressures during blood-filling. Without the vacuum relief means, the communication between the VAD and the pump inlet could result in the VAD being emptied of gas almost instantaneously, thus subjecting it thereafter to a too high vacuum, which would damage the membrane, or worse still, the blood itself. The vacuum relief means bleeds air or other gas into the pump inlet at a rate sufficient to avoid excessively low pressure developing in the VAD. Thus, the VAD is subjected to a suitable predetermined partial vacuum (i.e. a negative pressure).

The vacuum relief means may be any suitable such means known in the art.

One suitable form of vacuum relief means is a vacuum relief valve communicating between the pump inlet and the atmosphere, in parallel to the communication between the inlet and the VAD. The valve may be connected separately to the inlet, or may connect instead into the gas flow between the VAD and the inlet. Alternatively, a long, thin tube may be connected to the inlet, with its other end open to the atmosphere, to provide a suitably restricted air source.

The pump may comprise any pump which is able to provide suitable gas pressure, such as a vane-type pump, a blower-type pump or a compressor. The pump is preferably adapted and arranged to provide substantially smooth gas flow from its outlet to the VAD during blood emptying. In this way the pump outlet can be directly connected to the VAD without the need for intermediate buffering to smooth the gas flow to protect the VAD from pressure variations or other changes due to gas flow fluctuation.

In a preferred embodiment, the pump comprises a plurality of pistons driven by a single motor travelling at constant speed. This arrangement has a relatively low power requirement, whilst achieving smooth, suitable pressures and flow rates. The term "constant speed" is used herein to signify a speed which is substantially constant over one or more VAD beats, i.e. as distinct from the speed fluctuations of a reciprocating motor. The motor speed may be varied (such that same motor runs different "constant speeds"), for example to change the volume of air delivered by the compressor, but any such variation would be at a much lower frequency than that of the VAD pumping rate.

A single piston is not preferred due to uneven battery loading and pressure variations during the piston stroke. Three pistons arranged in parallel between the pump inlet and outlet are most preferred as this arrangement results in even loading on the battery and provides substantially constant, smooth pressures and gas flow.

The pump and switching valve may be controlled and powered by suitable electronics in the driver controller. Suitable valves (such as solenoid valves) may be used to connect the VAD gas supply line alternately to the outlet and inlet of the pump.

The outlet of the pump may be connected to the VAD gas supply line via the switching valve and a buffering plenum tank during blood-emptying, in order to smooth the gas flow and provide more even pressures, to protect the VAD, although in the preferred embodiment using a suitable pump, this is not required, thus saving further space and weight.

In the case of a piston-type pump, the gas discharge pressure and flow rate from the outlet to the VAD may be controlled by speed regulation of the pump motor.

The inlet of the pump may be connected to communicate directly to a VAD gas supply line, with the vacuum relief means also connected either into the supply line or separately to the pump inlet. However, in a preferred embodiment, the VAD communicates with the pump inlet via a negative pressure (partial vacuum) plenum chamber, which is also mounted on the housing, connected between the supply line and the pump inlet, with the vacuum relief means located so as to place the plenum chamber in communication with the atmosphere. The plenum chamber acts as a negative pressure reservoir and buffers the gas flow from the VAD to the pump inlet, thus smoothing any pressure fluctuations. This is especially important for gas flow from the VAD, as small pressure variations could cause relatively large changes in gas flow from the VAD because of its relatively small gas capacity and, thus, subject the VAD membrane to damaging vacuum pressures. The vacuum relief means allows the plenum chamber to "breathe" and thus prevents excessively low pressures being imparted to the VAD membrane during blood-filling.

In the embodiments of the present invention using a partial vacuum plenum chamber between the VAD and the pump inlet, it is most preferred to place the pump within that chamber. The plenum chamber may then serve as a reservoir of low pressure gas in direct, non-piped communication with the inlet port or ports of the pump. The gas flow from the VAD during blood-filling may be arranged to vent into the plenum chamber.

Locating the pump within the plenum chamber provides a number of important advantages. Firstly, a buffer in the air flow from the VAD is provided without any significant increase in size, as a chamber enclosing the pump is sufficiently large to provide an adequate buffering function. The partial vacuum in the plenum chamber also acts as a sound barrier, thus reducing the operating noise level of the pump. Gas flow within the plenum chamber over the pump acts to cool the moving parts, thus reducing the need for extra cooling equipment. The inlet port or ports of the pump do not have to be physically connected at all to the VAD gas supply line nor to the vacuum relief means, thus reducing the complexity of the valving and piping required in the system. This is especially significant when using piston type pumps, because making the necessary sealed connections to the piston inlets may be difficult.

The arrangement of a pump in a plenum chamber itself constitutes a new departure and may be applicable to arrangements where more than one pump is provided.

Thus, according to a second aspect of the present invention, there is provided a driver for at least one pneumatically-actuated ventricular assist device (VAD) comprising: a pumping system and valve arranged to supply gas flow to and from the at least one VAD for performing blood-emptying and blood-filling operations, the at least one VAD communicating with the inlet of the pumping system during blood-filling via a plenum chamber having vacuum relief means communicating with the interior of the chamber to maintain the chamber at a predetermined pressure; wherein the chamber encloses the pumping system.

For added convenience and compactness, the switching valves and, optionally, associated electronic controller may also be located within the plenum chamber. The valve may then open directly into the plenum chamber during blood-filling without the need for a piped outlet connection between the valve and pump. However, it is preferred to locate the battery power source in a separate compartment on the housing external of the plenum chamber, so that the batteries can be replaced easily and safely without interrupting the operation of the driver.

The outlet of the pump can preferably be off-loaded whenever it is not required to communicate with the VAD to empty it of blood, in order to conserve power. Preferably, the outlet is exhaustible to the atmosphere, and a silencer may be used to reduce noise levels.

If both the inlet and the outlet of the pump communicate with the VAD via plenum chambers, then two separate chambers must be provided and mounted on the housing, with the pump located within the low pressure, inlet-side chamber.

If two VADs requiring differing negative pressures (partial vacuums) on their membranes during blood-filling are being driven, then two low pressure plenum chambers, one for each VAD, may be used, to provide the different low pressures. The pump is located in one chamber and the other chamber communicates therewith via suitable valves between the two chambers to maintain the appropriate pressures.

In use, the VAD is driven by communicating it with the outlet of the pump for a set time of, for example, 300 ms to empty it, and then for the remaining time of the VAD pumping beat (e.g., 700 ms for a rate of 60 beats per minute) the VAD gas supply line is switched to communicate with the inlet of the pump to allow the VAD to fill with blood.

If two VADs are being used, they are preferably driven to empty consecutively, for example the second may be driven to empty, for the set period of time, immediately after the emptying of the first VAD has finished, and then be switched to fill for the remaining period of the beat and the emptying time of the first VAD on the next beat. In this manner the VADs are not emptied simultaneously, and thus a smaller pump can be used than in the case where both VADs are emptied simultaneously. The driving of the VADs need not be synchronous with the heartbeat. However, the VADs may be provided with sensors (e.g., Hall effect switches) to indicate when they are full of blood, such that emptying may be begun at that point. In this way, because exercise would increase the rate of blood flow to the VAD, the VAD system can effectively mimic the increase in heart rate as the patient exercises.

The driver preferably automatically operates the VADs. Suitable control algorithms can be used to optimise power usage and to provide responsiveness to the activity level of the patient.

Embodiments of the invention may have applications other than for a VAD.

Accordingly, viewed from a further aspect the invention provides a driver for at least one pneumatically-powered device, comprising a pumping system and a valve operable to alternately communicate an inlet and outlet of the pumping system with the at least one pneumatically-powered device in use, wherein the pumping system inlet is communicated with the device via a plenum chamber provided with a vacuum relief means, and wherein the plenum chamber houses at least one pump of the pumping system and, optionally, the valve.

A number of preferred embodiments of the present invention will now be described by way of example only and with reference to the accompanying FIGURE which shows schematically a portable pneumatic VAD driver according to the present invention.

As shown in the FIGURE, the driver comprises a low pressure partial vacuum plenum chamber 1 enclosing a pump 2 which is driven by a motor 3, which is also within the chamber 1. The pump 2 comprises an air compressor having a number of cylinders and the driving motor 3 may be, for example, a 12-volt DC motor.

The outlet 4 of the pump 2 is connected to a switching valve 5. The valve 5 can connect the outlet 4 of the pump directly via air supply line 6 to the leftside VAD 7, via line 8 to a second switching valve 9, or via line 10 to an exhaust 11 open to the atmosphere. The latter two connections are determined by the position of the switches 12, 12'.

The second switching valve 9 is operable to connect the line 8 to a second, rightside VAD 13 via air supply line 14, or to the exhaust 11 via line 15.

The switching valves 5 and 9 can take any suitable form, such as solenoid controlled valves which can be driven between different positions.

The inlet ports 29 of the pump open directly to the interior of the low pressure plenum chamber 1, which thus acts as a reservoir of low pressure air to the pump 2. A vacuum relief valve 16 communicates between the interior of the plenum chamber 1 and the atmosphere to maintain the plenum chamber at a suitable low pressure.

The valves 5 and 9 are operable to connect the gas supply lines 6 and 14 to the outlet 4 of the pump 2, or to open those lines to the low pressure interior of the chamber 1. In the latter case, the gas supply lines 6 and 14 are placed in non-piped communication with the inlet of the pump 2. This subjects the air chamber and membranes of the VADs 7 and 13 to the low pressure within the chamber 1.

The chamber 1 also encloses a suitable electronic microprocessor controller 17 for the driver, and a number of pressure transducers and other devices 18 for monitoring the operation of the driver and providing feedback to the controller 17. A safety relief valve 19 is provided at the outlet of the pump 2 to avoid excessively high pressures occurring at that outlet, and a further safety relief valve 20 is provided in communication with the atmosphere and the interior of the chamber 1 to avoid excessively low pressures occurring in the chamber.

The exhaust 11 may include a silencer, for example, a highly porous carbon cover.

An intake filter 21 is preferably mounted on the inlet of the vacuum relief valve 16 to ensure that the air within the chamber 1 is free of dust and other particulate impurities.

The power source for the motor and control electronics is provided in the form of batteries 22 which are contained in a separate compartment 23 which is electrically connected to the plenum chamber 1. Both a main battery pack and a reserve battery back may be provided. A connection 25 to an external power supply is also provided as a back-up.

The electrical compartment 23 may also include a communication port 26 for connection to a data gathering or processing device, such as a personal computer, for example, for monitoring the operation of the driver.

An audible alarm 27 may also be included and controlled to sound whenever any problem arises in the driver and an air bulb may be provided to drive the VAD manually in the event of failure of the pump in the driver.

The plenum chamber 1 and compartment 23 are both mounted on a housing which can be carried by the patient.

Operation of the driver will now be described, considering firstly the case in which only a single VAD is being driven, i.e. the left VAD 7 shown in the FIGURE.

We shall use, as an example, a beat rate for the VAD of about 60 beats per minute.

At the start of a beat the VAD 7 is connected to the outlet 4 of the pump 2 by moving the valve 5 to the position shown in the FIGURE. This supplies pressurised air in the direction 31 via lines 4, 6 to the air space in the VAD 7 thus forcing the membrane to empty the VAD of blood. The pressurised air is supplied to the VAD to empty it for a fixed period of time of between about 250–300 milliseconds.

Once that period has ended, the valve 5 is switched to the left (when looking at the FIGURE) so as to open the VAD line 6 to the interior of the plenum chamber 1, such that air flows from the VAD in the direction 30, and to connect the outlet of the pump 2 via the line 10 to the exhaust 11 (the switches 12, 12' being respectively opened and closed). This arrangement is maintained for the remainder of the beat (e.g., another 700 milliseconds). During that time the outlet of the pump 2 is off-loaded to the atmosphere by the exhaust 11, thus conserving power, and the air chamber of the VAD is connected to the low pressure plenum chamber 1, thus drawing blood into the VAD to fill it.

At the end of the filling period the valve 5 is switched to its original position to supply high pressure air to the VAD to empty it, thus recommencing the cycle.

The motor 3 driving the pumping system 2 is preferably driven at a constant speed of about 4500 rpm. Its speed may be varied to control the air discharge pressure and flow rate to the VAD during blood-emptying.

A suitable pressure on the VAD membrane for blood-emptying is about 300 mm Hg and during blood-filling a suitable pressure is about −40 mm Hg.

The VAD 7 may be provided with a sensor (not shown) to detect when it is full, and the driver can be controlled to empty the VAD as soon as the full signal is detected.

As the blood-emptying period is set to be constant, in the case of differing beat rates the blood-filling period will vary accordingly.

In the case of driving both VADs 7 and 13, the first VAD 7 is emptied for about 300 milliseconds as above, and after that period it is connected to the air plenum chamber 1 to fill it, as before. However, the outlet 4 of the pump 2 once it has emptied the left VAD 7 is connected to the second control valve 9 via the line 8, rather than to the exhaust 11, by suitable positioning of the switches 12, 12'.

The valve 9 is then placed in the position shown in the FIGURE to connect the outlet 4 to the supply line 14 to provide high pressure air to the right VAD 13 to empty it of blood. Again the right VAD 13 is emptied for fixed period of time of about 250–300 milliseconds. Once the right VAD emptying time has finished, the valve 9 is switched to the left so that the outlet 4 of the pump 2 is connected via line 15 to the exhaust 11, and the VAD 13 and line 14 are connected directly to the interior of the chamber 1, thus subjecting the VAD 13 to low pressure to fill it with blood, in the same manner as for the left VAD 7.

Both VADs then fill for the remainder of the beat, and once the next beat commences, the valve 5 is switched to empty the left VAD 7, whilst the valve 9 is maintained in position to continue filling the right VAD 13. Once the left VAD 7 has emptied and is beginning to fill, the valve 9 is switched to empty the right VAD 13, and so on.

When driving the two VADs in the above manner, it can be seen that each VAD is emptied in the period whilst the other VAD is filling, such that the output from the pump and the available time is used efficiently.

Of course, if a driver for only a single VAD is required, the second valve 9 and its associated connections and controls may be omitted.

In an alternative embodiment of the present invention, the pump 2, motor 3, valves 5, 9 and associated components are placed outside the vacuum plenum chamber 1 (which therefore contains only the vacuum relief valve 16) and the inlet 29 of the pump 2 is instead in piped direct communication with the chamber 1. This arrangement allows an enhanced cooling airflow over the pump and motor to be maintained. This improved cooling may be desired if two VADs are being driven simultaneously, as in that case there would be greater heat generation by the pump 1 and motor 2, which may be too great to control satisfactorily if it occurs within the vacuum plenum chamber 1 (i.e. if the components are all located within the plenum chamber 1 as in the first embodiment).

It can be seen that the single pump necessary for the present invention and the corresponding reduction in battery requirement results in a significantly smaller and lighter pneumatic VAD driver. The driver is both compact and light enough to be readily portable and can be mounted on a wheeled trolley, for example, or preferably mounted on a housing to be worn or otherwise carried by the patient.

In a preferred arrangement, the pneumatic VAD driver of the present invention is built into a housing in the form of an outer padded bag with straps to enable a patient to wear the unit over his or her shoulder, complete with microprocessor controller and a self-contained battery power source. This enables the patient to be transported by car or ambulance, or to walk about and take physical exercise with the VAD or VADs operated entirely from a portable shoulder bag. This is clearly preferable to larger bedside trolley-mounted console-type VAD drivers and enhances greatly the patient's quality of life.

Although the present invention has been described with reference to pneumatically-actuated VADs, it is envisaged that the driver unit may have application in other areas. For example, it could be used to drive a pneumatically actuated-artificial heart, which operates in place of, rather than to assist the natural heart, or to drive other pneumatically actuated devices. The driver of the present invention is also applicable in any situation in which both low and high pressures are required to be supplied by a portable unit, including any such applications outside the medical field.

One example of a non-medical application is to drive a tethered crawler for examining the insides of small bores or pipes. The crawler is powered by a peristaltic propulsion unit in which two bladders alternately inflate and deflate, whilst simultaneously axially extending and retracting, to provide forward or reverse motion. The driver of the present invention could be used in this system to provide the gas flow to inflate and deflate the bladders.

We claim:

1. A blood pumping system, comprising:
   at least one pneumatically-actuated ventricular blood pumping device, a portable housing, the housing mounting: a single pump arranged to generate gas flow for performing both blood-filling and blood-emptying operations of the at least one blood pumping device, wherein the pump has an inlet and an outlet, and a switching valve for alternately directly communicating the gas flow from the inlet and outlet of the pump with the at least one blood pumping device, the blood pumping system further comprising vacuum relief means communicating with the inlet of the pump so that the blood pumping device is subjected to a predetermined negative pressure when performing blood-filling, and a controller for controlling operation of the pump and the switching valve.

2. A system as claimed in claim 1, wherein the vacuum relief means comprises a vacuum relief valve arranged to provide the communication between the inlet of the pump and the atmosphere.

3. A system as claimed in claim 1 further comprising means for providing substantially smooth gas flow from the pump outlet to the blood pumping device during blood-emptying whereby the pump outlet may be connected directly to the blood pumping device without intermediate buffering of the gas flow.

4. A system as claimed in claim 1, wherein the pump comprises a single motor traveling at constant speed, and a plurality of pistons arranged to generate gas flow, the plurality of pistons being driven by the single motor.

5. A system as claimed in claim 4, wherein the pump comprises three pistons between the pump inlet and outlet arranged to generate their gas flow in parallel to thereby provide substantially constant pressure and gas flow.

6. A system as claimed in claim 1, further comprising a plenum chamber mounted on the housing and wherein the blood pumping device communicates with the pump inlet via the plenum chamber.

7. A system as claimed in claim 6, wherein the plenum chamber has an interior and the vacuum relief means is located so as to communicate the interior of the plenum chamber with the atmosphere.

8. A system as claimed in claim 6, wherein the plenum chamber encloses the single pump.

9. A system as claimed in claim 8, wherein the plenum chamber has an interior and the inlet to the pump is in direct non-piped communication with the interior of the plenum chamber.

10. A system as claimed in claim 8, wherein the plenum chamber further encloses the switching valve and controller.

11. A system as claimed in claim 1, further comprising means for off-loading the outlet of the pump when not performing blood-emptying.

12. A system as claimed in claim 1, wherein the housing further comprises means for enabling a patient to carry the system.

13. A system as claimed in claim 12, wherein the housing includes at least one carrying strap.

14. A system as claimed in claim 12, further comprising a bag with straps and wherein the housing is contained within the bag to enable the system to be carried by a patient.

15. The device of claim 1, wherein the pneumatically actuated ventricular blood pumping device is a pneumatically-actuated ventricular assist device (VAD).

16. A system as claimed in claim 15, further comprising means for driving two VADs simultaneously.

17. A system as claimed in claim 16, further comprising means for performing blood-emptying for each VAD consecutively.

18. The system of claim 1, wherein the pneumatically-actuated ventricular blood pumping device is an artificial heart.

19. A driver for use with at least one pneumatically-actuated ventricular blood pumping device, the driver comprising a portable housing, the housing mounting: a single pump having an inlet and an outlet, the pump being arranged to generate gas flow which is capable of performing both blood-filling and blood-emptying operations of the at least one pneumatically-actuated ventricular blood pumping device, the driver further comprising a switching valve arrangeable to alternately communicate the inlet and outlet of the pump with the at least one pneumatically-actuated ventricular blood pumping device in use, vacuum relief means communicating with the inlet of the pump for ensuring that the at least one blood pumping device is subjected to a predetermined negative pressure when performing blood-filling and a controller for controlling the operation of the driver, the driver further comprising a separate compartment mounted on the housing and a power source which is operatively associated with the pump, switching valve and controller and located in the separate compartment.

20. A pneumatically-actuated ventricular blood pumping system, comprising at least one pneumatically-actuated ventricular blood pumping device, a driver for the at least one pneumatically-actuated ventricular blood pumping device, the driver comprising: a pumping system having an inlet and an outlet, a valve arranged to supply gas flow directly to and from the pumping system to and from the at least one pneumatically-actuated ventricular blood pumping device for performing blood-emptying and blood-filling operations, a plenum chamber, the at least one pneumatically-actuated ventricular blood pumping device directly communicating with the inlet of the pumping system during blood-filling via the plenum chamber, and vacuum relief means communicating with the interior of the chamber to maintain the chamber at a predetermined pressure; wherein the chamber encloses the pumping system.

21. A method of driving at least one pneumatically-actuated ventricular blood pumping device, comprising:

driving a single pump, the pump having an inlet and an outlet, to thereby generate gas flow for performing both blood-filling and blood-emptying operations of the at least one pneumatically-actuated ventricular blood pumping device; alternately establishing direct gas flow from the inlet and outlet of the pump with the at least one blood pumping device by means of the switching valve to perform the blood-filling and the blood-emptying operations of the at least one blood pumping device; selectively communicating the inlet of said pump with vacuum relief means so that the at least one blood pumping device is subjected to a predetermined negative pressure when performing blood-filling; and mounting the single pump, switching valve and vacuum relief means on a portable housing.

* * * * *